(12) United States Patent
Voskuilen et al.

(10) Patent No.: US 10,849,778 B2
(45) Date of Patent: Dec. 1, 2020

(54) ANKLE-FOOT ORTHOSIS

(71) Applicant: NEA International B.V., Maastricht-airport (NL)

(72) Inventors: Agnes Theodora Maria Voskuilen, Maastricht-airport (NL); Anne Lie Ing Yap, Maastricht-airport (NL)

(73) Assignee: NEA International B.V.

(*) Notice: Subject to any disclaimer, the term of this patent is extended or adjusted under 35 U.S.C. 154(b) by 349 days.

(21) Appl. No.: 15/308,814

(22) PCT Filed: May 4, 2015

(86) PCT No.: PCT/NL2015/050305
§ 371 (c)(1),
(2) Date: Nov. 3, 2016

(87) PCT Pub. No.: WO2015/170973
PCT Pub. Date: Nov. 12, 2015

(65) Prior Publication Data
US 2017/0165094 A1  Jun. 15, 2017

(30) Foreign Application Priority Data

May 5, 2014  (NL) .................................... 2012754

(51) Int. Cl.
*A61F 5/01* (2006.01)
(52) U.S. Cl.
CPC ........... *A61F 5/0113* (2013.01); *A61F 5/0111* (2013.01)

(58) Field of Classification Search
CPC .. A61F 5/00; A61F 5/01; A61F 5/0102; A61F 5/14; A61F 5/0195; A61F 5/0113; A61F 5/0111; A61F 5/0104
USPC ........................................................... 602/28
See application file for complete search history.

(56) References Cited

U.S. PATENT DOCUMENTS

| 5,067,486 | A | * | 11/1991 | Hely | ................... | A61F 13/066 |
| | | | | | | 602/27 |
| 5,376,068 | A | | 12/1994 | Grifka | | |
| 5,472,414 | A | * | 12/1995 | Detty | ................... | A61F 5/0111 |
| | | | | | | 128/871 |
| 5,700,237 | A | | 12/1997 | Hess | | |
| 6,793,640 | B1 | | 9/2004 | Avon | | |

(Continued)

FOREIGN PATENT DOCUMENTS

| DE | 202011107040 U1 | 3/2012 |
| FR | 2993452 A1 | 5/2015 |

(Continued)

*Primary Examiner* — Tarla R Patel
(74) *Attorney, Agent, or Firm* — Woodard, Emhardt, Henry, Reeves & Wagner, LLP

(57) ABSTRACT

An ankle-foot orthosis includes a plantar flexion limiting device that limits the plantar flexion of the foot and which is configured to provide support for a user's foot drop. The ankle-foot orthosis includes a lower leg shell including a foot support and a lower leg support, and is configured to position and/or fix a user's heel in the lower leg support. The plantar flexion motion of the foot is limited by the complementary action of elastic and non-elastic portions of the plantar flexion limiting device. The plantar flexion limiting device further leads to a dynamic return of the foot to an angle substantially equal to the angle value $\alpha_2$.

20 Claims, 6 Drawing Sheets

(56) References Cited

U.S. PATENT DOCUMENTS

| 8,512,269 | B1 * | 8/2013 | Stano | A61F 5/0111 |
|---|---|---|---|---|
| | | | | 602/27 |
| 2007/0060854 | A1 | 3/2007 | Cropper | |
| 2010/0256544 | A1 | 10/2010 | Colon | |

FOREIGN PATENT DOCUMENTS

| NL | 1014794 | 10/2001 |
|---|---|---|
| WO | WO 2004/078076 A1 | 9/2004 |

* cited by examiner

ANKLE-FOOT ORTHOSIS

The invention relates to an ankle-foot orthosis which comprises means that limit plantar flexion and which is designed to provide support for a user's foot drop.

Foot support devices that limit plantar flexion are generally known. U.S. Pat. No. 5,376,068 A discloses an ankle joint brace comprising a frontal leg shell and a dorsal leg shell, which are pivoted together in an L-shape. The shell is fastened to a user's heel by means of an instep strap and a heel band. An elastic tensioning strap extends from the front part of the frontal leg shell from a first side of the frontal leg shell, over the instep, to a second side of the frontal leg shell opposite the first side for fixing the foot in place, from which position the tensioning belt extends over the front side of the ankle to the side of the dorsal leg shell on the first side. This tensioning strap is relatively ineffective with users with serious dorsiflexion paralysis, for example in the case of "complete" foot drop, because this tensioning strap only exerts a relatively large restoring force on the foot at relatively large angles between the foot and the lower leg.

DE 202011107040 U1 shows an orthopaedic device wherein the foot is supported on an insole element and wherein two elastic straps or two inelastic straps extend crosswise over the foot from opposite sides of the insole element near the front part of the foot to opposite sides of a device that is provided around the ankle. The device is provided with a spring element, so that said device can be easily arranged around the ankle. If the straps are elastic, the foot will be dynamically pulled up, whilst in the case of inelastic straps the foot will be held relatively static in a pre-set angle relative to the lower leg. Like the above-described ankle braced, this orthopaedic device is not suitable for users with serious dorsiflexion paralysis.

It is an object of the present invention to provide an improved ankle-foot orthosis by means of which in particular a relatively natural stride and preferably greater user comfort in comparison with the prior art can be realised.

In order to achieve that object the invention provides an ankle-foot orthosis according to claim 1. In use, a user's lower leg abuts the elongate lower leg support of the lower leg shell. At least part of the metatarsus, the region near the ball of the foot, is supported by the foot support. The foot support is configured to support a user's foot during at least the part of the stride when the metatarsus (or the corresponding part of the orthosis or the shoe) is clear of the ground. This part of the stride covers at least the period from "toe off" up to and including the "terminal swing".

During use, a user's heel is positioned and/or fixed in the lower leg shell by the heel fixing means. During use, the heel fixing means continuously drive the user's heel in the direction of a corner point that is determined by the foot support and the lower leg support. When, for example, an upright, L-shaped lower leg shell is used, the heel fixing means push the heel downward and rearward to the angle of the "L" shape. In this way the heel is prevented from losing contact with the lower leg shell during the stride. Preferably, the heel fixing means force the rear side of the heel against the end of the lower leg support that faces the foot support, as a result of which the heel is essentially prevented from moving forward, out of the lower leg shell. Preferably, the heel fixing means at the same time push the heel downward onto the lower leg portion of the lower leg support in use. In this way the heel is tightly fixed against the lower leg shell during the stride.

The angle $\alpha$ between the foot support and the lower leg support can be changed, i.e. it can change under the influence of a load during use, so that the foot support can at least partially pivot toward and away from the lower leg support. The foot support and the lower leg support are flexibly connected together, such that said angle $\alpha$ can be increased or decreased under load, for example upon movement of a user.

Using the non-elastic plantar flexion limiting means, the foot support, with the foot supported thereon, can be positioned at an angle with an angle value of $\alpha_2$ relative to the lower leg support with the lower leg abutting against it. The non-elastic plantar flexion limiting means are fixedly connected to the foot support, for example, wherein a user pivots the lower leg support until the angle $\alpha$ has the desired value $\alpha_2$ and subsequently fixes the non-elastic plantar flexion limiting means to the lower leg support in such a manner that the foot support is biased or at least set at a desired angle $\alpha_2$ relative to the lower leg support. Following that, the elastic plantar flexion limiting means are fitted in such a manner that they are biased at an angle $\alpha_2$.

After the angle $\alpha_2$ has been set, the non-elastic plantar flexion limiting means impede any further increase of the angle $\alpha_2$. Impede means that the non-elastic plantar flexion limiting means to a large extent hamper any further increase of the angle $\alpha$ but do not prevent it entirely. In other words, when the angle value $\alpha_2$ is exceeded, the foot experiences a significant force at least in the opposite direction of the angle $\alpha$, which opposes any further increase of the angle $\alpha$.

The angle value $\alpha_2$ set by the user determines when the elastic plantar flexion limiting means are activated. When the foot support is pivoted relative to the lower leg support during use, such that the value of the angle $\alpha$ is greater than the angle value $\alpha_2$, the elastic plantar flexion limiting means will stretch and the bias on the elastic plantar flexion limiting means will increase. The elastic plantar flexion limiting means thus biased force the foot support, and with it the foot, back to an angle $\alpha$ which is essentially equal to the angle value $\alpha_2$. In one embodiment the elastic plantar flexion limiting means thus pull the foot support essentially upward and toward the lower leg support when the angle value $\alpha_2$ is exceeded.

The elastic plantar flexion limiting means are configured so that they impede movement through an angle $\alpha$ greater than $\alpha_2$, to be true, but significantly less so than do the non-elastic plantar flexion limiting means. The effect achieved with the elastic plantar flexion limiting means is that a relatively natural foot strike is realised. Preferably, the extent to which the foot is forced back to an angle $\alpha$ substantially equal to the angle value $\alpha_2$ will increasingly become stronger as the angle $\alpha$ increases to a value beyond the angle value $\alpha_2$, so that a further increase of the angle $\alpha$ requires a greater effort each time the angle $\alpha$ increases by one degree.

An additional advantage is that the elastic plantar flexion limiting means contribute to a dynamic limitation of the increase of the angle $\alpha$ beyond the angle value $\alpha_2$. This dynamic limitation can be realised in a simple manner by forming the elastic plantar flexion limiting means from an elastic material. It is conceivable that also the non-elastic plantar flexion limiting means partially contribute to returning the foot after the angle $\alpha_2$ has been exceeded. Likewise, the elastic plantar flexion limiting means can contribute toward initially impeding the exceeding of the angle $\alpha$ beyond the angle $\alpha_2$.

From the prior art only ankle-foot orthoses comprising elastic plantar flexion limiting means are known. In addition to that there are ankle-foot orthoses comprising non-elastic plantar flexion limiting means. In other words, the non-elastic and the elastic plantar flexion limiting means are considered to be alternatives, and the choice one of these alternatives will be based on the medical indication. The present invention is based on the idea that the two types of plantar flexion limiting means are complementary to each other rather than being alternatives to each other, and that the elastic plantar flexion limiting means can thus be combined with non-elastic plantar flexion limiting means. The present invention is different from the prior art in that elastic as well as non-elastic plantar flexion limiting means are provided in an ankle-foot orthosis, so that the foot strike, for example in the case of foot drop, will become as near to a natural foot strike as possible. The object of the present invention is thus achieved.

FR 2993452 (A1) shows an orthopaedic device for stabilising an ankle joint, comprising a partially rigid sole that is pivoted at right angles to lateral uprights. The lateral uprights are connected to the sole by elastic straps so as to limit the extent of plantar flexion. The orthopaedic device is intended for use in a shoe and does not comprise any heel fixing means and foot support fixing means: the shoe positions the foot in the orthopaedic device during the stride.

WO 2004078076 (A1) describes an ankle brace comprising a sole which is connected to a heel counter by means of a click arrangement. Elastic straps for limiting the plantar flexion connect the heel counter to the sole. A shoe is needed for keeping the foot positioned on the ankle brace during, since the ankle brace itself is not provided with heel fixing means and foot support fixing means.

U.S. Pat. No. 6,793,640 (B1) shows an ankle apparatus comprising a first body with a support portion for a sole which is orthogonally connected to a second body comprising a support portion for a heel. Inelastic straps connect the first body to the second body for limiting the plantar flexion. A shoe is needed for using the ankle apparatus, as the ankle apparatus is unable to position and/or fix a user's heel and foot in the orthopaedic apparatus without the use of a shoe.

U.S. Pat. No. 5,700,237 (A) discloses a therapeutic device comprising an L-shape with a leg portion that is pivotally connected to a foot support portion. Inelastic straps extend between the leg portion and the foot support portion for limiting the extent of plantar flexion. The foot is fixed on the L-shape by means of an anklet and an ankle strap. This therapeutic device is not intended for use without a shoe.

None of the aforesaid four documents shows a combination of elastic and non-elastic plantar flexion limiting means. An additional distinction between those documents and the ankle-foot orthosis according to the present invention is the configuration of the heel fixing means, which make it possible to use the ankle-foot orthosis in a shoe but also without a shoe. The four aforementioned documents only describe devices for use either with a shoe or without a shoe.

In particular, the construction of the non-elastic and the elastic plantar flexion limiting means is configured so that said means can limit the extent of plantar flexion without this interfering, at least not to a significant degree, with a decrease of the angle $\alpha$ to a value lower than the angle value $\alpha_2$. In other words, an increase of the angle $\alpha$ to a value beyond the angle value $\alpha_2$, the so-called plantar flexion, is limited, but a decrease of said angle $\alpha$ (wherein $\alpha<\alpha_2$), is not impeded. It is conceivable, however, to configure the plantar flexion limiting device so that it will return the foot to an angle $\alpha$ substantially equal to the angle value $\alpha_2$ also upon dorsiflexion of the foot.

Preferably, the lower leg shell is resilient, such that it can spring back to an angle $\alpha_1$ after an increase or a decrease of the angle $\alpha$ in relation to the angle $\alpha_1$ which lies within the range of possible $\alpha_2$ values, so that the lower leg shell can be biased to the angle $\alpha_2$ by the non-elastic plantar flexion limiting means.

In one embodiment, the foot support is modeled on at least part of the foot. It is conceivable that the foot support will support only part of the underside of the foot, leaving the toes clear, for example, so as to provide greater freedom of movement.

In one embodiment, the non-elastic plantar flexion limiting means are configured to perform the function of the heel fixing means as well. The non-elastic plantar flexion limiting means position and/or fix also the heel of the foot in the lower leg shell. Preferably, the non-elastic plantar flexion limiting means extend over the foot in such a manner that the non-elastic plantar flexion limiting means exert a force on the foot which drives the heel against the lower part (in use) of the lower leg support, as well as a force on the foot which limits the extent of plantar flexion when the angle $\alpha_2$ is exceeded. Such a configuration can be realised in a simple manner by means of a substantially inelastic material which is stretched over the foot in such a manner that the foot is pressed into the lower leg support in use, and also by providing an inelastic connection between the foot support and the lower leg support, the tension on which inelastic connection increases when the angle $\alpha_2$ is exceeded. It is conceivable in that regard that the elastic plantar flexion limiting means contribute to the function of the heel fixing means. The addition of the function of the heel fixing means to the non-elastic plantar flexion limiting means results in a compact embodiment of the ankle-foot orthosis according to the present invention, which can be used both in a shoe and without a shoe.

In one embodiment, the ankle-foot orthosis further comprises foot support fixing means, for example in the form of a non-elastic or an elastic strap that extends over the foot from both sides of the foot support. In use, the front end (in use) of the footrest can be tightly fixed to the underside of the foot when use is made of the foot support fixing means. The foot is positioned and/or fixed to the foot support in such a manner that it essentially abuts the underside of the foot during the stride. Preferably, the foot support fixing means extend over the foot, or in particular over the instep of the foot. Preferably, the foot support fixing means extend from one long side of the foot support to the other, opposite long side of the foot support. It is conceivable that the foot support fixing means allow at least part of the underside of the foot to come clear of the foot support during parts of the stride, so that the foot support does not unnecessarily interfere with a smooth stride.

In one embodiment, the non-elastic plantar flexion limiting means are configured to perform the function of the foot support fixing means as well. The non-elastic plantar flexion limiting means in that case extend from a front part (in use) of the foot support, over the foot, to the lower leg support. Thus there is no need for separate foot support fixing means. In particular, the non-elastic plantar flexion limiting means and the elastic plantar flexion limited means perform the function of the heel fixing means as well as that of the foot support fixing means. According to the user's needs, additional foot support fixing means and/or lower leg support fixing means may be provided on the ankle-foot orthosis according to the present invention.

In an advantageous embodiment, two or more of the above-mentioned features are according to the invention combined in one functional element. Preferably, the non-elastic plantar flexion limiting means also perform the function of the elastic plantar flexion limiting means in use.

In one embodiment, the ankle-foot orthosis further comprises lower leg support fixing means by which the end of the lower leg support remote from the foot support (the upper end in use) can be fixed tightly to the lower leg. Preferably, the lower leg support fixing means are provided in the form of a substantially non-elastic strap, which extends partially around the lower leg from the upper part (in use) of the lower leg shell.

In one embodiment, the lower leg support fixing means are configured to perform the function of the plantar flexion limiting device as well. The non-elastic plantar flexion limiting means and/or the elastic returning means in that case extend further along at least the front side of the lower leg in use, so that they are pressed against the lower leg support.

In one embodiment, the elastic plantar flexion limiting means are configured to perform the function of the foot support fixing means as well. In use, the elastic plantar flexion limiting means extend over the foot in such a manner that the elastic plantar flexion limiting means press the foot onto the foot support. In a simple embodiment, the elastic plantar flexion limiting means are provided in the form of at least part of an elastic stocking.

Using the above combinations of two or more functions in a single element, a simple and compact orthosis is obtained. The combined function of parts of the orthosis will be discussed in more detail hereinafter.

Preferably, the angle value $\alpha_2$ can be set between 80° and 100°; preferably it is around 90°. The ankle-foot orthosis thus comes near the user's natural posture when the user is standing upright. It is conceivable to set different values for the biasing angle $\alpha_2$ in dependence on a user's requirements and circumstances.

In one embodiment, the non-elastic plantar flexion limiting means form a connection between the foot support and the lower leg support in use, such that this connection will only transmit a force between the foot support and the lower leg support when the angle $\alpha$ exceeds the angle value $\alpha_2$. This force contributes to limiting any further increase of the angle $\alpha$ (the plantar flexion). In the case of angles larger than the angle value $\alpha_2$, the non-elastic plantar flexion limiting means become slack, as it were, so that the angular motion at $\alpha<\alpha_2$ is not impeded. This does not stand in the way of decreasing the angle between the foot (support) and the heel (support), so that the stride, in particular during the strike of the foot during the part of the stride from "mid stance" to "heel off" will hardly be impeded unnecessarily, if at all. This essentially unimpeded dorsiflexion contributes toward a stride that feels natural. In one embodiment of the present invention, the non-elastic plantar flexion limiting means are made up of at least one substantially inelastic connection between the foot support and the lower leg support in use. In one example, the ends remote from each other of the foot support and the lower leg support are connected by an inelastic connection. The inelastic connection is preferably capable of deformation to such an extent that it will not impede a decrease of the angle between the foot support and the lower leg support.

In one embodiment, the connection of the non-elastic plantar flexion limiting means between the foot support and the lower leg support is formed by at least one non-elastic strap. The length and possibly adjustable position in use of the strap determine the adjustable angle value $\alpha_2$. After placing a foot in the orthosis, a user can pivot the lower leg support relative to the foot support to an angle with the desired angle value $\alpha_2$, whereupon the user will attach the non-elastic strap to the foot support and the lower leg support, so that, in the absence of a further load, the angle value $\alpha$ will remain the same as the adjusted angle value $\alpha_2$.

When the angle $\alpha$ becomes larger in use, reaching the angle value $\alpha_2$, the tension on the non-elastic strap will further increase, thereby impeding a further increase of the angle $\alpha$. Preferably, also the elastic plantar flexion limiting means will come into action in that case so as to further impede the increase of the angle and return the foot to an angle $\alpha$ substantially equal to the angle value $\alpha_2$. In this way the extent of plantar flexion is limited. The non-elastic strap is preferably capable of deformation to such an extent that the angle $\alpha$ can be decreased without any interference from the strap. As a result, the dorsiflexion is not hampered by the non-elastic strap.

Preferably, the at least one non-elastic strap is configured to partially extend crosswise from one side of the foot support, over the foot, to the other side opposite the one side of the foot support. In use, the non-elastic strap engages one side of the foot support and extends over the foot to the other, opposite side of the foot support.

Such an embodiment, which closely abuts the foot, makes it possible to use the orthosis in a shoe but also without a shoe. The shoe may be an orthopaedic shoe, but it may also be a shoe as generally known. In addition to that, the non-elastic strap that crosses the foot has a positioning and/or fixing function for the foot in the lower leg shell, for example for pressing/positioning/fixing a user's foot on the foot support. The plantar flexion limiting device can thus also be used as a foot support fixing means. This fixation of the foot is very advantageous when the orthosis is used without a shoe.

Preferably, an attachment for the non-elastic strap is provided on the other side of the foot support. This attachment may be an opening, a hook or a loop, for example. In one embodiment, the at least one non-elastic strap is configured to extend in part substantially parallel to the lower leg support. From the attachment, the at least one non-elastic strap extends along or over the lower leg support in use. In one embodiment, a first fastener for a non-elastic strap is provided at the end of the lower leg support remote from the foot support for realising a detachable attachment of the at least one non-elastic strap to the lower leg support, for example using VELCRO®, a hook or other known means of attachment. It is conceivable that, in use, the at least one non-elastic strap does not extend along the lower leg support but along a user's shinbone.

In one embodiment, the non-elastic plantar flexion limiting means comprise at least two non-elastic straps which are connected to the foot support on either side thereof. The at least two non-elastic straps extend from opposite sides of the foot support, preferably near the front part of the foot in use, to the lower leg support. It is possible to have the at least two non-elastic straps cross over the foot in use.

Preferably, fasteners are provided on either side of the ankle joint in use, through which the at least two non-elastic straps extend. The fasteners are for example configured as fastening eyes or fastening slots. From the fasteners, the at least two non-elastic straps extend parallel to the lower leg support.

Preferably, the at least two non-elastic straps are connected at one end. In particular, a detachable means of attachment is provided at said connected end, which can be detachably connected to the lower leg support by means of the first fastener for a non-elastic strap. Such an embodiment comprising at least two non-elastic straps increases the stability for a user. The at least two crossing non-elastic straps provide in particular not only a force perpendicular to the plane of the foot support, but also a lateral (seen from a user's viewpoint) force.

In one embodiment, the foot support is configured so that it closely abuts the foot during the entire stride of the foot. To enhance user comfort, the foot support is flexible. During a stride, the foot support can deform such that it is in contact with the sole of the foot. This dynamic abutment between foot and foot support enhances user comfort, in particular when the orthosis is used without a shoe. The foot support may be modeled on at least part of the foot.

A preferred embodiment is provided with a rear foot support portion configured to support the underside of a heel of a foot. This is preferably the part of the lower leg shell on which the heel is positioned and/or fixed by the heel fixing means. The rear foot support portion extends substantially transversely to and from the lower leg support in the direction of the foot support and is flexibly connected thereto. During a stride, a user's heel is relatively static in relation to the orthosis. The rear foot support portion is preferably rigidly connected to the lower leg support for positioning and/or fixing the heel of the foot in the lower leg shell.

The foot support is flexibly and movably connected to the rear foot support portion. In particular, side walls are provided on either side of the ankle joint in use, which side walls extend between the rear foot support portion and the lower leg support. Fasteners for the at least one non-elastic strap may be provided on the side walls. The side walls, the lower leg support and the rear foot support portion thus form a space within which at least a user's heel can be stably positioned and/or fixed. Such a construction leads to a firm orthosis exhibiting sufficient flexibility for realising a stride that feels natural.

In one embodiment, the elastic plantar flexion limiting means are elastic in use, to such an extent that when the angle value $\alpha$ increases beyond the angle value $\alpha_2$, said means will exert a force that drives back the foot to an angle $\alpha$ substantially equal to the angle value $\alpha_2$. As the angle $\alpha$ increases, the elastic plantar flexion limiting means exert an increasing force on the foot, so that it will take an increasing effort to further increase the angle $\alpha$. The elastic plantar flexion limiting means thus contribute toward limiting the extent of plantar flexion, which can be realised in a simple manner by providing an elastic connection between the foot support and the lower leg support. Especially advantageous is that the elastic plantar flexion limiting means are also configured for dynamically returning the foot to an angle $\alpha$ substantially equal to the angle value $\alpha_2$, preferably in that the elastic plantar flexion limiting means are set to return to their starting shape when the foot makes an angle $\alpha$ substantially equal to the angle value $\alpha_2$ with the lower leg. The elastic plantar flexion limiting means may be biased to such an extent that they will exert a force on the foot in the case of an angle $\alpha$ smaller than the angle value $\alpha_2$. This force from the elastic plantar flexion limiting means also contributes toward limiting the plantar flexion. In addition to that, the elastic plantar flexion limiting means may be biased so that they at least partially perform or complement the function of a user's lower leg dorsiflexors in the case of an angle $\alpha$ smaller than $\alpha_2$, so that a user with foot drop, for example, will be able to raise his or her foot to an angle $\alpha$ smaller than $\alpha_2$.

Very advantageous is the complementary effect of the non-elastic and elastic plantar flexion limiting means, wherein the non-elastic plantar flexion limiting means deliver the initial force on the foot for the plantar flexion limitation when the angle $\alpha$ becomes substantially equal to the angle value $\alpha_2$, wherein subsequently, at angles $\alpha$ greater than the angle value $\alpha_2$, the elastic plantar flexion limiting means add a complementary force on the foot for the plantar flexion limitation, which force increases as the angle $\alpha$ increases. In this way the forces exerted on the foot during the stride are effectively taken up by the orthosis.

Preferably, the elastic plantar flexion limiting means comprise at least two elastic straps connected to the foot support, which straps extend crosswise over the foot in use. The elastic straps each engage one of the opposing sides of the foot support, extending crosswise over the instep of the foot. Preferably, the elastic plantar flexion limiting means extend over the front side of the foot in that case.

Preferably, the elastic straps are further detachably connected to a second fastener for an elastic strap on opposite sides of the lower leg support in use, in particular at halfway the height of the lower leg support. The detachable connection enables the user to bias the elastic straps according to his or her own needs. The user can thus set a magnitude of the restoring force and the point at which said force will come into action.

In addition to that, this crossing embodiment of the elastic plantar flexion limiting means offers an additional stabilising action, because it is capable of transmitting a moment about an axis in a user's forward direction in addition to a moment about an axis in the lateral direction.

Said elastic straps are preferably detachable, so that a user can quickly and easily step into the lower leg shell without any encumbrance from the straps, after which the elastic straps can be set to the required bias in a simple operation.

Preferably, the lower leg shell is open at the front side, such that the user can quickly step into and out of the shell. In particular, no parts of the lower leg shell extend along the front side (shinbone) of the lower leg and the foot during said stepping in and out. To make it possible to position and/or fix the lower leg rapidly in the orthosis, it is conceivable that side portions on either side of the lower leg shell are configured to abut the sides of a lower leg. Said side portions in particular abut the lower leg for positioning and/or fixing it in the lower leg shell. After the lower leg has been positioned and/or fixed in the lower leg shell, the lower leg can preferably be secured in the orthosis by a simple closure of the foot support fixing means, the elastic plantar flexion limiting means and/or the non-elastic plantar flexion limiting means, which are in particular configured to extend, preferably at least partially, along the front side of the lower leg and the foot.

In a compact embodiment, the non-elastic straps at least in part perform the function of the foot support fixing means as well as the heel fixing means. Preferably, the non-elastic straps also contribute to the function of the foot support fixing means. Thus, the non-elastic straps are provided crosswise over the foot, for example, and position and fix the foot on the foot support. In addition to that, the non-elastic straps force the heel into its position in the lower leg shell and thus form the heel fixing means. The elastic and non-elastic straps together form the plantar flexion limiting device according to the present invention. The individual aspects thus provide the desired effect. When combined, the aspects can reinforce one another.

In a preferred embodiment, the ankle-foot orthosis further comprises an inversion limiting device for preventing a foot from twisting inward, seen from a user's viewpoint. In addition to that it is possible for the ankle-foot orthosis to further comprise an eversion limiting device for preventing the foot from twisting outward, seen from a user's viewpoint. Thus a user's stability is increased in that twisting of the foot is prevented. These functions, too, can be performed in different ways, possibly as an additional function of an already mentioned aspect or in combination therewith.

Preferably, the plantar flexion limiting device performs the function of the inversion limiting device and/or the eversion limiting device. The crossing straps of the plantar flexion limiting device can for example take up a tilting moment in the transverse (from the user's viewpoint) direction (the left-right direction). Because the plantar flexion limiting device extends obliquely over the foot from the left-hand side of the foot support to the right-hand side of the ankle, the plantar flexion limiting device comprises an effective lever arm, as it were, both in the longitudinal direction of the foot (the forward direction) and in the transverse direction of the foot (the left-right direction). The plantar flexion limiting device thus enhances a user's stability in the forward direction and in the transverse direction.

In particular, one of the crossing non-elastic straps of the plantar flexion limiting device forms the inversion limiting device, and the other of the crossing non-elastic straps forms the eversion limiting device. In the above-described manner, the non-elastic straps counteract inversion and/or eversion. The eversion and/or inversion limiting device can thus be readily made up of the plantar flexion limiting device. It is further conceivable for the inversion limiting device and/or the eversion limiting device to be provided separately from the plantar flexion limiting device.

In an advantageous embodiment, the foot support fixing means, the heel fixing means, the lower leg support fixing means, the elastic and/or the non-elastic plantar flexion limiting means can be detachably connected to the lower leg shell for realising a quick and simple attachment to the lower leg shell. Preferably, such an attachment comprises a VELCRO®, buttons or books, so that the position of the attachment on the lower leg support is adjustable.

In one embodiment, an opening is provided in the lower leg support, near the foot support, for at least the heel of the foot so as to provide a close abutment of the lower leg shell to a user's heel. Because of the provision of the opening, a lower leg fitted with an orthosis according to the invention will be relatively slimmer for use in a standard shoe. The heel fixing means make it possible to use the ankle-foot orthosis according to the present invention also without a shoe.

In one embodiment, the lower leg support fixing means comprise a lower leg strap on the upper side of the lower leg support in use, which lower leg strap extends substantially horizontally around the lower leg, so that the lower leg can be fixed against the lower leg support in a quick and simple manner.

The present invention will be explained in more detail below with reference to the appended figures, in which.

Identical elements are as much as possible indicated by the same numerals in the description below. To avoid unnecessary repetition, such elements are not introduced anew in every drawing.

Figure 1:
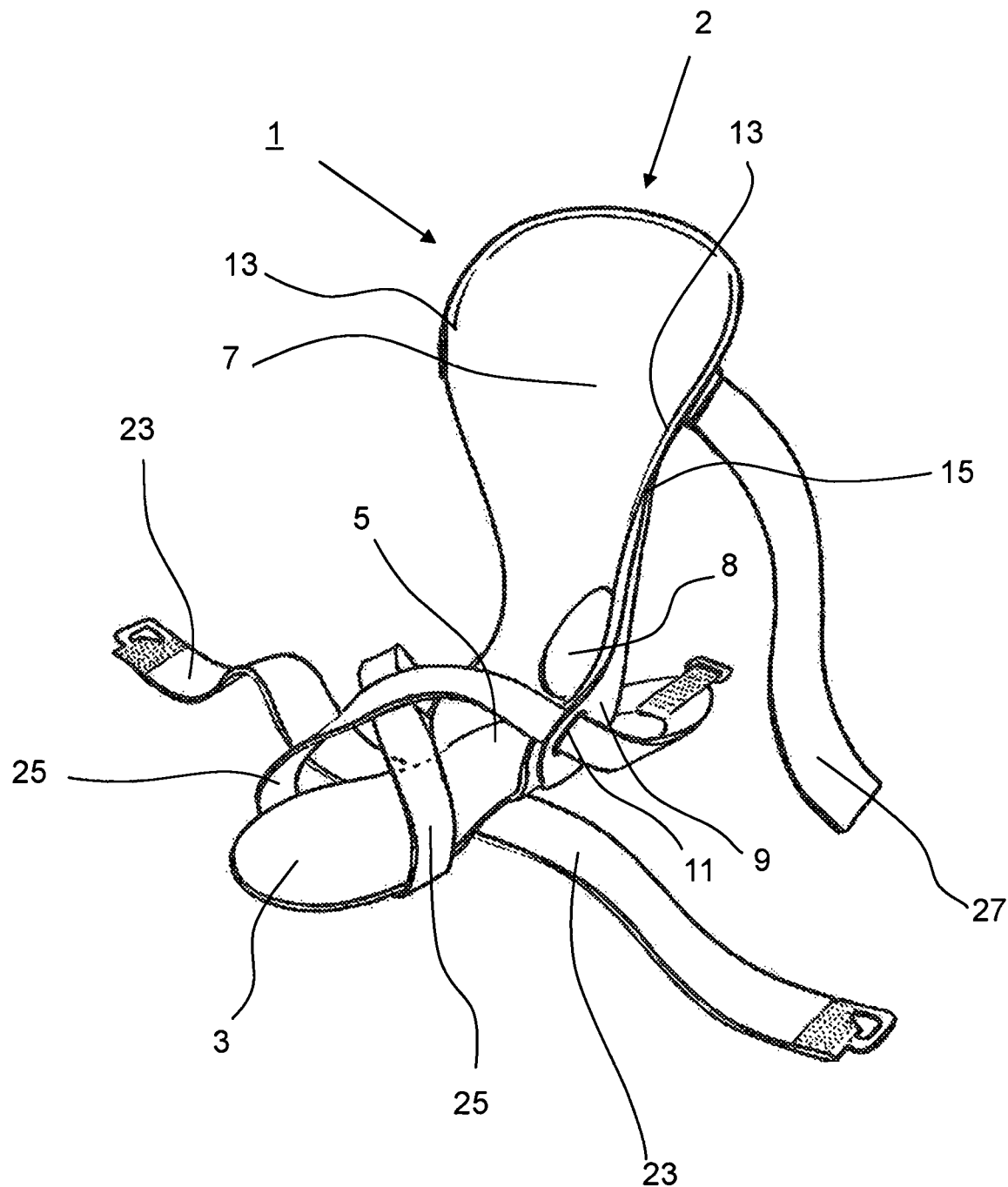
FIG. 1 is a perspective view of an ankle-foot orthosis according to the present invention in the open position for receiving a lower leg.

FIG. 1 shows in perspective view an ankle-foot orthosis 1 according to the present invention in the open position for receiving a lower leg 21 (not shown in FIG. 1) in the lower leg shell 2 thereof. The foot support 3 is preferably modelled on the shape of a user's foot. The foot support 3 is preferably thin so as to make it possible to use the orthosis 1 in combination with a shoe (not shown). The foot support 3 is connected to the rear foot support portion 5, which is positioned under the rear portion of a user's foot in use. The rear foot support portion 5 can extend up to the rear side of the lower leg in use, but it is also possible for the rear foot support portion 5 to extend up to a position is spaced from the rear side of the lower leg. The heel opening 8 also extends on the underside of the heel of the foot 21a in that case. The rear foot support portion 5 and the foot support 3 preferably form one plane, which is substantially identical to the shape of the sole of the user's foot. In one embodiment, the foot support 3 leaves clear the underside of at least the toes.

In FIG. 1, the lower leg support 7 extends in vertical direction from the rear foot support portion 5, substantially perpendicular to the foot support 3. The lower leg support 7 is connected to the rear foot support portion 5. This connection is preferably a rigid connection. In use, side walls 9 are provided between the rear foot support portion 5 and the lower leg support 7 on either side of a user's ankle. Each side wall 9 is provided with an opening 11. As shown in FIG. 1, the lower leg support 7 widens in upward direction, so that the side portions 13 of the lower leg support 7 extend partially around the lower leg 21. Seen from a user's viewpoint, the lower leg support 7 is positioned substantially behind the lower leg 21, with the side portions 13 of the lower leg support 7 positioned to the left and to the right of the lower leg 21. Thus, also the side walls 9 can be placed substantially to the left and to the right of the ankle 21b and/or the heel. A second fastener 15 for an elastic strap 23 is provided on each of the side portions 13 of the lower leg support 7. At the rear side of the lower leg support 7, a first fastener 17 for a non-elastic strap is provided. A third fastener 19 (which is not shown in FIG. 1, but whose position is broadly indicated at 19 in FIG. 4) for a lower leg strap 27 is provided at the top of the lower leg support 7 of the orthosis 1 in FIG. 1. This third fastener 19 for a lower leg strap 27 is preferably formed by VELCRO®, buttons, hooks or a slot through which the lower leg strap 27 can extend.

In FIG. 1, the upper side of the lower leg support 7 is connected to a lower leg strap 27 which is configured to function as lower leg support fixing means 27. The lower leg strap 27 is fixedly connected to the lower leg support 7 at one end and can be detachably connected to the third fastener 19 for a lower leg strap 27 at another end.

A non-elastic strap 25 is attached to both sides (left-hand side and right-hand side, seen from a user's viewpoint) of the foot support 3, near the front side of the foot support 3. Each non-elastic strap 25 extends from its attachment to the foot support 3 to the opening 11 in the side wall 9, which is located on the side of the foot support 3 opposite the attachment to the foot support 3. In other words, one non-elastic strap 25 extends from its attachment on the left-hand side of the foot support 3 to an opening 11 on the right-hand side of the foot support 3, whilst the other non-elastic strap 25 extends from the right-hand attachment to the left-hand opening 11. At some point the non-elastic straps 25 cross one another. The non-elastic straps 25 further extend through the openings 11, behind which the non-elastic straps 25 are connected together at their ends. The connected ends of the non-elastic straps 25 can be connected to the first fastener 17 for a non-elastic strap 25.

Between the attachments of the non-elastic straps 25 and the lower leg support 7, in particular the rear foot support portion 5, two elastic straps 23 extend from the foot support 3 on opposite sides of the foot support 3. One elastic strap 23 is connected to the left-hand side of the foot support 3, whilst the other elastic strap 23 is connected to the right-hand side of the foot support 3. The elastic straps 23 can be connected to the elastic strap fasteners 15.

Figure 2:
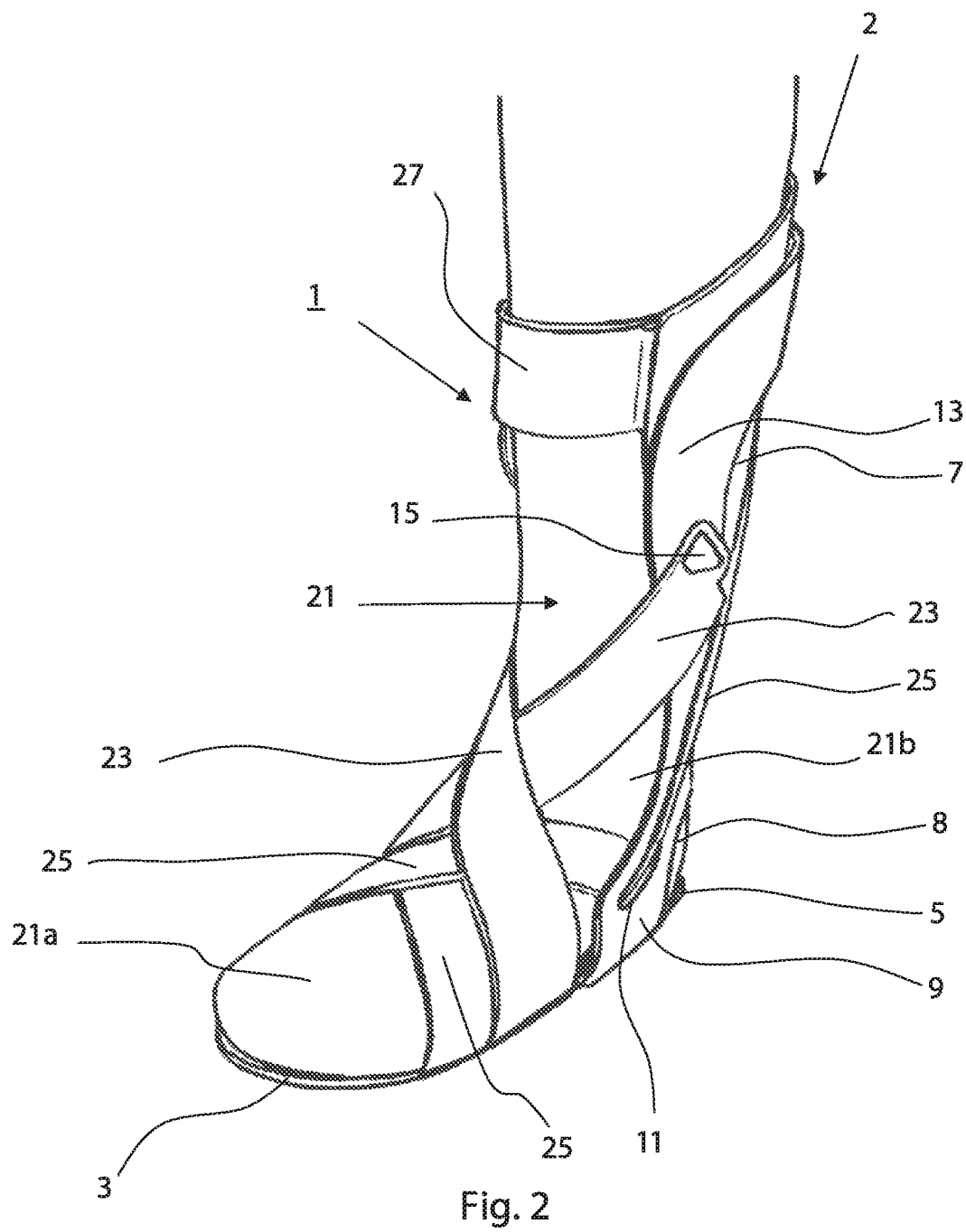
FIG. 2 is a perspective view of an ankle-foot orthosis according to the present invention during use thereof.

FIG. 2 shows in perspective view an ankle-foot orthosis 1 according to the present invention during use. A lower leg 21 is placed in the lower leg shell 2 in such a manner that the rear side of the lower leg 21 closely abuts the lower leg support 7. The foot 21a rests on the foot support 3, with the rear portion of the foot 21a positioned on the rear foot support portion 5. The heel and part of the ankle 21b of the foot 21 are in part enclosed by the side walls 9.

The lower leg strap 27 extends substantially horizontally around the lower leg 21. In FIG. 2, the lower leg strap 27 is fixed to the lower leg support 7 with one end and detachably connected to the third fastener 19 for a lower leg strap 27 with the other end, for example by means of VELCRO®. The position of the lower leg strap 27 on the third fastener 19 for a lower leg strap 27 can be adjusted for realising a close abutment at varying circumferential dimensions of the lower leg 21.

The non-elastic straps 25 form the non-elastic plantar flexion limiting means. Each non-elastic strap 25 can be connected to the first fastener 17 for a non-elastic strap 25 of the lower leg support 7 in such a manner that there will be a tension on the non-elastic strap 25. The adjusted position on the lower leg support 7 and the thus defined length of the non-elastic straps 25 determine the angle value $\alpha_2$ for the angle $\alpha$ between the foot support 3 and the lower leg support 7. By attaching the non-elastic straps 25 at a higher position on the lower leg shell, the bias on said straps 25 will be increased. After being attached to the lower leg support 7, the non-elastic straps 25 effectively impede an increase of the angle $\alpha$, which increase is known as plantar flexion. At an angle $\alpha$ equal to the angle value $\alpha_2$, the non-elastic straps are capable of compensating the relatively large reactive force exerted on a foot being placed on the ground. It is possible to adjust the angle value $\alpha_2$ by changing the position of the fastener of the non-elastic straps 25 on the lower leg support 17. A lower position, in use, preferably results in an increase of the angle value $\alpha_2$.

A decrease of the angle $\alpha$ is not impeded by the non-elastic straps 25. When the foot support 3 pivots toward the lower leg support 7, the tension is released from the non-elastic straps 25. The non-elastic straps 25 than become slack, as it were, so that the foot support 3 can pivot in the direction of the lower leg support 7 without being impeded. Dorsiflexion of the ankle 21b is thus not impeded by the orthosis 1. A user wearing the orthosis 1 according to the present invention can still freely move his or her knee forward, so that the stride will feel natural. In addition to that, a user can thus get up more easily, for example from a chair.

In use, the non-elastic straps 25 extend over the foot 21a, thereby positioning and/or fixing the foot 21a on the foot support 3. The non-elastic straps 25 thus also form the foot support fixing means by which the end of the foot support 3 remote from the lower leg support can be placed into close abutment with the foot 21a.

The non-elastic straps 25 further form the heel fixing means. The non-elastic straps 25 position and fix the foot 21a in the lower leg shell 2 during the stride in that the non-elastic straps 25 are just themselves to the foot 21a during the stride. The user thus has freedom of movement without the position of the foot 21a in the lower leg shell 2 being lost. In addition to that it is conceivable for the non-elastic straps 25 to contribute toward returning the foot to an angle $\alpha$ substantially equal to the angle value $\alpha_2$ when the angle $\alpha$ exceeds the angle value $\alpha_2$. Use can be made in this regard of the shape-retaining property of the lower leg shell 2. Upon deformation of the lower leg shell 2 in the case of an increase of the angle $\alpha$ beyond the angle value $\alpha_2$, the lower leg shell 2 will exert a reactive force against the movement of the deformation, which reactive force can be transmitted to the foot 21a by the non-elastic straps 25 for driving back the foot 21a to an angle $\alpha$ substantially equal to the angle value $\alpha_2$.

As FIG. 2 shows, two elastic straps 23 are arranged over the non-elastic straps 25 and the foot 21a. The elastic straps 23 are attached to opposite sides of the foot support 3, one elastic strap 23 on the left-hand side and the other elastic strap 23 on the right-hand side of the foot support 3. The elastic straps 3 each extend from their attachment to the foot support 3 to the opposite side of the foot support 3, i.e. one elastic strap 23 from the left to the right and the other elastic strap 23 from the right to the left. The elastic straps 23 are arranged over the non-elastic straps 25.

The elastic straps 23 form the elastic plantar flexion limiting means. As shown in FIG. 2, the elastic straps 23 cross on the instep. The elastic straps 23 can furthermore be detachably connected to the second fastener 15 four and the elastic strap 23 on the sides 13 of the lower leg support 7, for example by means of VELCRO®, buttons, hooks or other known means of attachment. The elastic straps 23 can thus be biased to a desired value by adjusting the position of the connection to the second fastener 15 for an elastic strap 23. The relative strength of the force by which the elastic straps return the foot to an angle $\alpha$ substantially equal to the angle value $\alpha_2$ can thus be adjusted by the user himself, if desired.

When the angle value $\alpha_2$ is exceeded, the elastic straps 23 will return the foot 21a to an angle $\alpha$ substantially equal to the angle value $\alpha_2$. In use, the elastic straps 23 form an elastic connection between the foot support and the lower leg support 7. When the angle $\alpha$ increases beyond a predetermined angle value, which may equal $\alpha_2$, the elastic straps 23 will stretch to such an extent as to exert a force that urges the foot support 3 and the lower leg support 7 toward each other. This force causes the foot 21a to return to an angle $\alpha$ substantially equal to the angle value $\alpha_2$. As the angle $\alpha$ increases, this force will become stronger as a result of the elastic straps 23 being stretched further. The elastic straps 23 thus form the elastic plantar flexion limiting means for realising a smooth strike of the foot 21a and a dynamic return of the foot 21a to an angle $\alpha$ substantially equal to the angle value $\alpha_2$. At an angle $\alpha$ substantially equal to the angle value $\alpha_2$, the foot takes up the position of the foot 21a shown in FIG. 2, in which FIG. 2 the angle value $\alpha_2$ is about 90°.

Figure 3:
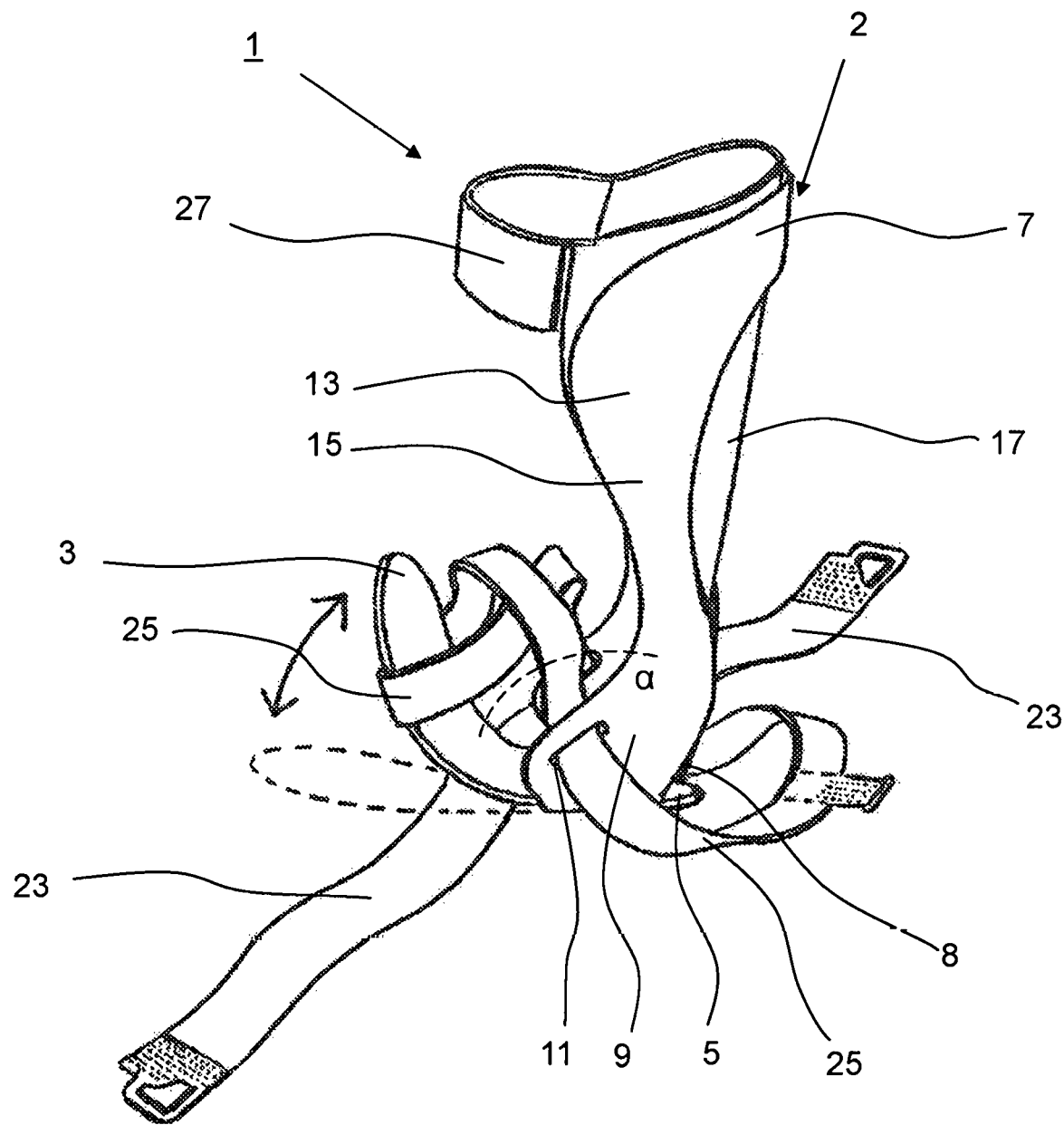
FIG. 3 is a side view of an ankle-foot orthosis according to the present invention, in which the angle α is smaller than the angle value $α_2$.

FIG. 3 shows a side view of an ankle-foot orthosis according to the present invention, in which the foot support 3 is bent in relation to the rear foot support portion 5. The toot support 5 essentially makes an angle with the vertical direction in FIG. 3, in which FIG. 3 the angle is less than $\alpha_2$, viz. about 45°.

When the heel is placed on the ground, the foot 21 will experience a downward "slapping" moment. While walking, a user first places his heel on the ground, keeping the foot 21a away from the ground surface. This phase of the gait cycle is known as the "initial contact". Upon touching the ground surface, the foot experiences a reactive force of a magnitude of about seven times the user's body weight. This reactive force leads to a moment of force on the foot 21a, causing it to pivot about an axis in a user's lateral direction, which axis is located in or near the ankle 21b. This lever effect forces the foot 21a to "slap". A user with foot drop is not able to take up these forces.

The non-elastic straps 25 according to the present invention are capable of taking up at least a significant part of the initial slap of about seven times the body weight. The elastic straps 23 also contribute, to a lesser extent, toward taking up this "slap" and in addition to that dynamically return the foot to the neutral position. As a result, the stride will feel and look more natural when the orthosis 1 according to the present invention is used. In addition to that, the orthosis 1 according to the present invention leads to an energy-efficient stride.

FIG. 3 shows the flexibility of the foot support 3, which enables the foot support 3 to closely abut the foot 21a during the stride. The foot support 3 is configured so that it can deform so as to continuously conform to the shape of the sole of the foot without this causing any discomfort to the user.

The orthosis 1 according to the present invention further contributes toward reducing the inversion and eversion (sideways twisting of the foot 21a). Because the non-elastic straps 25 extend from one side of the foot support to the opposite side of the foot support 3, they are capable of taking up an inversion and/or eversion movement. When, for example, a left foot 21a twists inward in a so-called inversion movement, the tension on at least the non-elastic strap 25 that is connected to the left-hand side of the foot support 3 will increase. This non-elastic strap 25 thus limits the extent of twisting by transmitting a tilting moment opposed to the inversion movement to the foot support 3. The non-elastic straps 25 thus increase the stability for a user.

Figure 4:
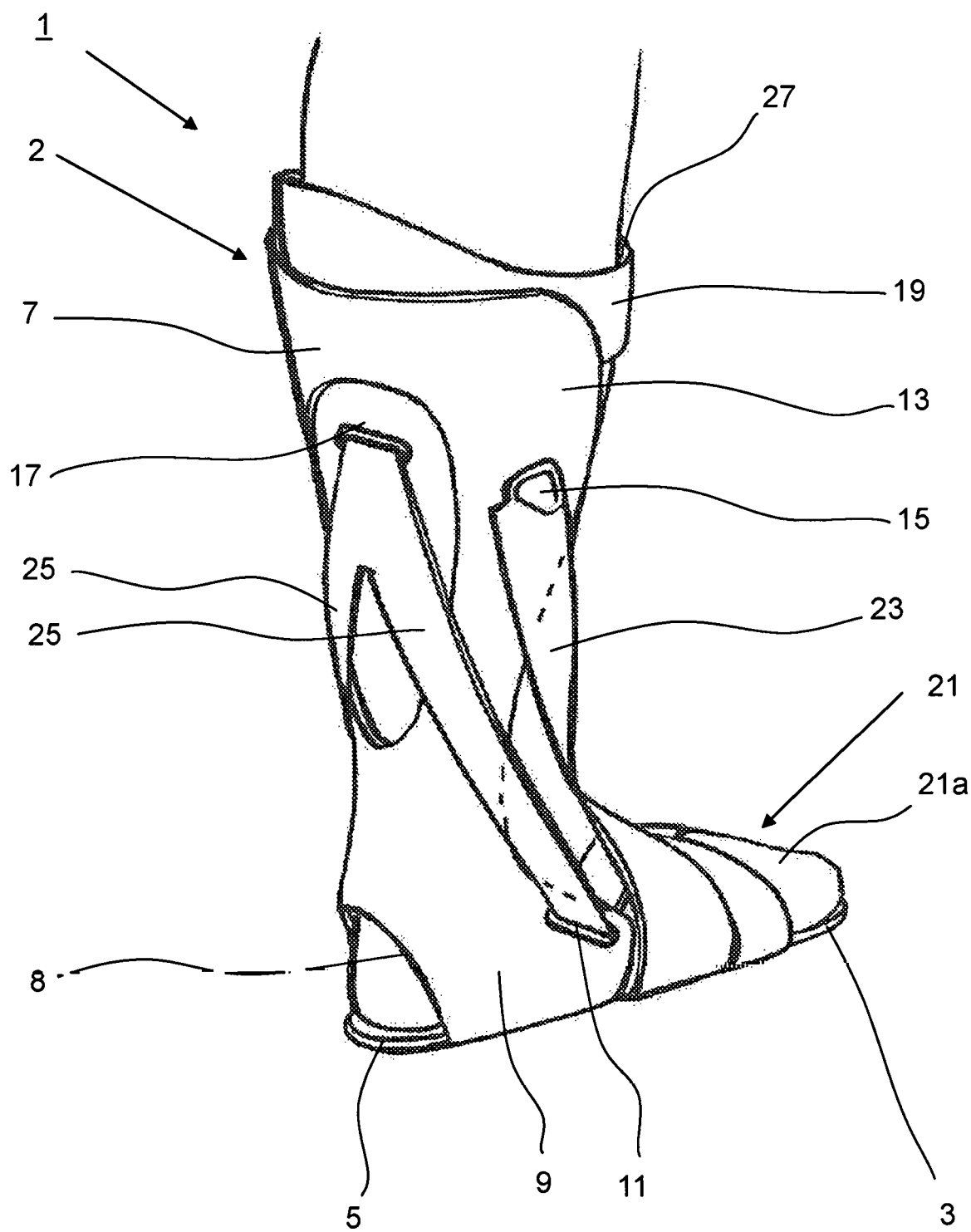
FIG. 4 is a perspective view of a rear side of an ankle-foot orthosis according to the present invention.

FIG. 4 shows the rear side of an orthosis 1 according to the present invention. A heel opening 8 is provided in the lower leg support 7. The opening 8 is oval in shape in this exemplary embodiment so as to provide a proper abutment of the lower leg shell 2 against a user's heel.

Figure 5:
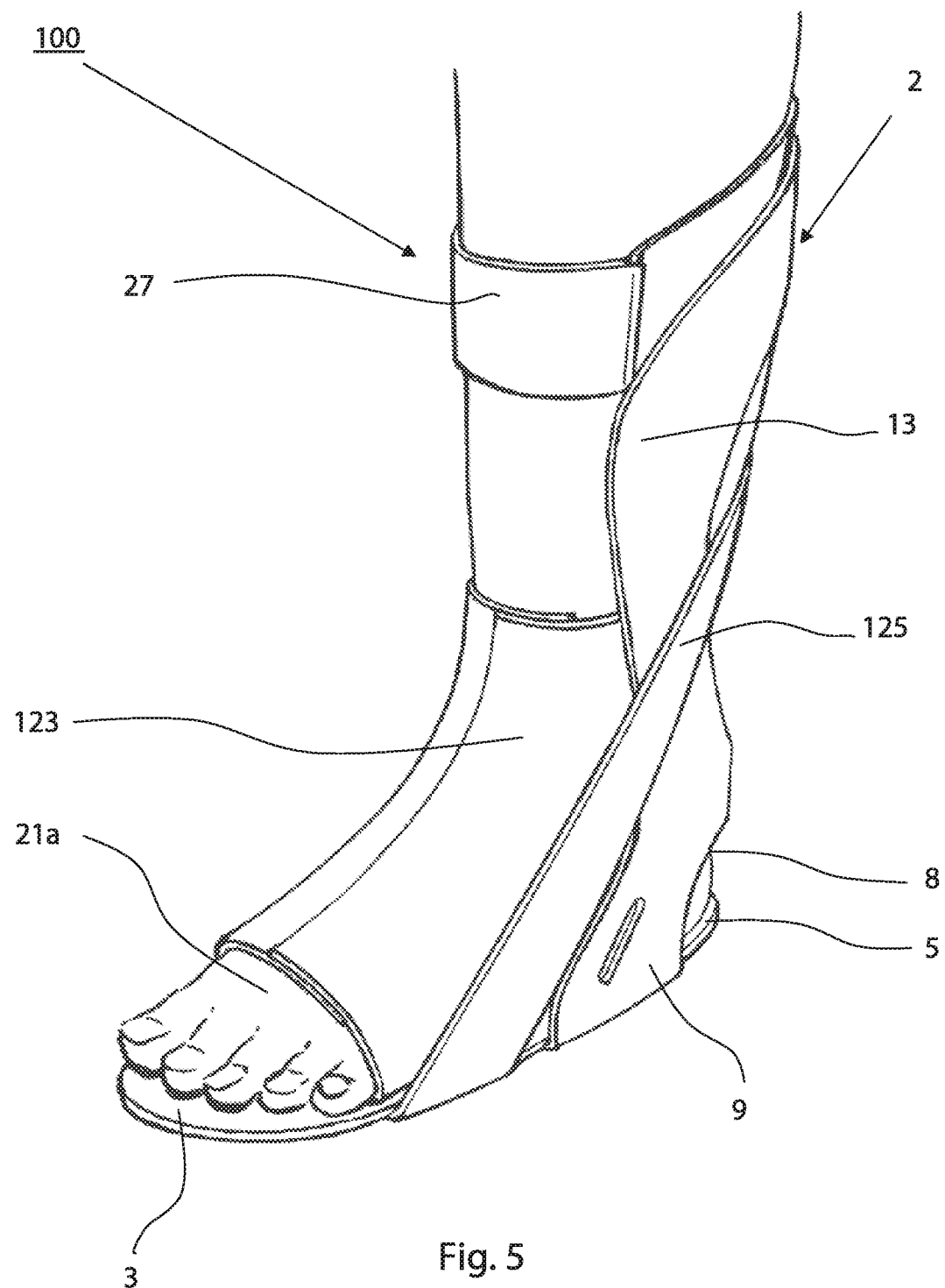
FIG. 5 is a perspective view of an embodiment of an ankle-foot orthosis according to the present invention, in which the non-elastic straps are arranged substantially parallel to each other.

FIG. 5 shows in perspective view an embodiment of an ankle-foot orthosis 1 according to the present invention, in which the non-elastic straps 125 are arranged substantially parallel to each other. Each non-elastic strap 125 extends from its attachment to the foot support 3, along one side of the foot 21a, to a first fastener 17 for a non-elastic strap 25. The non-elastic strap 125 that is attached to the left-hand side of the foot support 3 extends along and over the left-hand side of the foot 21a to the first fastener 17 for a non-elastic strap 25.

The elastic plantar flexion limiting means 123 are configured as a tight-fitting envelope 123 of the foot 21a. The envelope 123 is an elastic stocking, for example, which is connected to the lower leg shell 2. The envelope 123 is accessible to a foot 21a via a re-closeable closure on the front side of the envelope 123.

Figure 6:
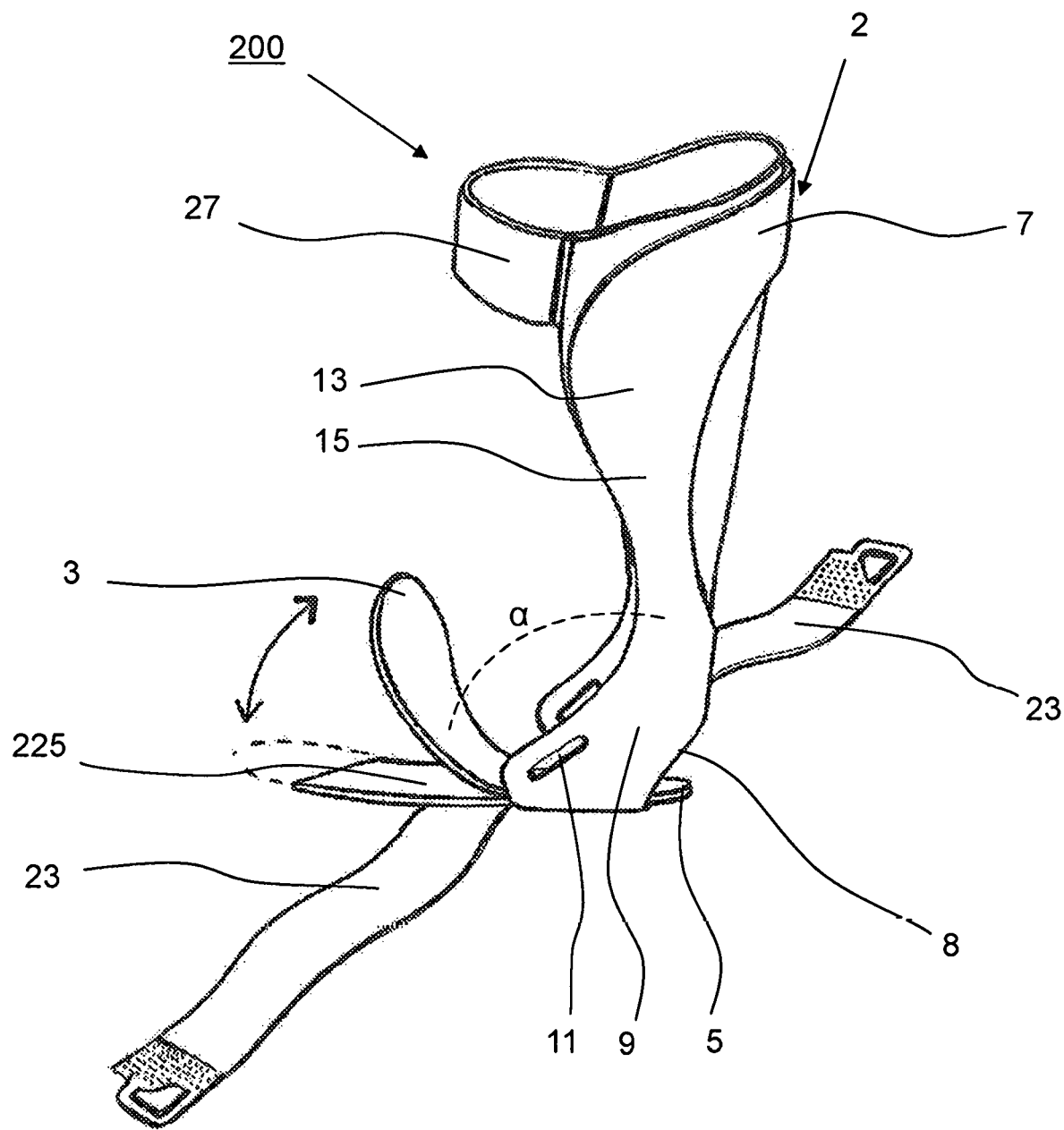
FIG. 6 is a side view of an embodiment of an ankle-foot orthosis according to the present invention, in which the non-elastic plantar flexion limiting means are provided on the underside of the foot support.

FIG. 6 shows a side view of an embodiment of an ankle-foot orthosis 200 according to the present invention, in which the non-elastic plantar flexion limiting means 225 are provided under the underside of the foot support. A rigid plate 225 extends forward under the foot support 3, transversely to the lower leg support 7. The plate 225 is rigid to such an extent that it can impede pivoting of the foot support 3 beyond an angle $\alpha_2$.

In the foregoing, the invention has been described with reference to a few exemplary embodiments. Those skilled in the art will appreciate that many modifications and alternatives are possible within the scope of the invention. The invention is not limited to these exemplary embodiments, however. The protection sought is defined by the appended claims.

The invention claimed is:

1. An ankle-foot orthosis for providing support for a user's foot drop, comprising:
   a substantially L-shaped lower leg shell having an elongate lower leg support configured to be placed against a rear side of a user's lower leg and an elongate foot support configured to support at least part of an underside of a metatarsus, said lower leg support and foot support are oriented at an adjustable angle $\alpha$ relative to each other;
   a plantar flexion limiting device which is configured to allow a smooth foot strike of a foot of the user supported by the ankle-foot orthosis, said plantar flexion limiting device having a substantially non-elastic portion and a substantially elastic portion, wherein the non-elastic portion is configured to impede the angle $\alpha$ exceeding an angle value $\alpha_2$ and wherein the elastic portion is configured to effect a dynamic return of the user's foot to an angle $\alpha$ equal to the angle value $\alpha_2$ when the angle $\alpha$ exceeds the angle value $\alpha_2$;
   wherein said non-elastic portion of said plantar flexion limiting device includes a first non-elastic strap attached to said lower leg shell and a second non-elastic strap attached to said lower leg shell, and wherein an end of said first non-elastic strap and an end of said second non-elastic strap are connected together so that the connected ends are in contact with each other;
   wherein the connected ends of said first non-elastic strap and said second non-elastic strap are attachable to a fastener on said lower leg support, and wherein the position of the connected ends on the fastener is adjustable to modify the angle value $\alpha_2$; and
   wherein said plantar flexion limiting device is configured to position and/or orient a user's heel in the lower leg support.

2. An ankle-foot orthosis according to claim 1, wherein the non-elastic portion is configured to position and/or orient a user's heel in the lower leg support.

3. An ankle-foot orthosis according to claim 1, wherein the plantar flexion limiting device is configured to fix an end of the foot support that is remote from the lower leg support to the foot of the user.

4. An ankle-foot orthosis according to claim 3, wherein the non-elastic portion is configured to fix the end of the foot support that is remote from the lower leg support to the foot of the user.

5. An ankle-foot orthosis according to claim 3, wherein the elastic portion and the non-elastic portion can at least in part be detachably connected to the L-shaped lower leg shell.

6. An ankle-foot orthosis according to claim 1, wherein the non-elastic portion is configured to effect a dynamic return of the user's foot to an angle $\alpha$ substantially equal to the angle value $\alpha_2$ when the angle $\alpha$ exceeds the angle value $\alpha_2$.

7. An ankle-foot orthosis according to claim 1, wherein the ankle-foot orthosis further comprises a lower leg support fixing device by which an end of the lower leg support that is remote from the foot support can be fixed tightly to the lower leg.

8. An ankle-foot orthosis according to claim 1, wherein the angle value $\alpha_2$ substantially ranges between 80° and 100°.

9. An ankle-foot orthosis according to claim 1, wherein the non-elastic portion forms a connection between the foot support and the lower leg support in use, such that this connection will only transmit a force between the foot support and the lower leg support when the angle $\alpha$ exceeds the angle value $\alpha_2$.

10. An ankle-foot orthosis according to claim 9, wherein the connection of the non-elastic portion between the foot support and the lower leg support is formed by at least one of said first non-elastic strap and said non-elastic second strap, whose shape and positioning determine the adjustable angle value $\alpha_2$ in use.

11. An ankle-foot orthosis according to claim 10, wherein at least one of the first non-elastic strap and the second non-elastic strap is configured to partially extend crosswise from one side of the foot support, over the foot, to an other side opposite the one side of the foot support.

12. An ankle-foot orthosis according to claim 11, wherein said first non-elastic strap is attached to one side of the foot support and said second non-elastic strap is attached to the other side opposite the one side of the foot support.

13. An ankle-foot orthosis according to claim 1, wherein the lower leg support and the foot support are connected by means of a rear foot support portion configured to support an underside of a rear part of a foot, wherein the rear foot support portion extends substantially transversely to the lower leg support in a direction of the foot support, at the angle $\alpha$ equal to the angle value $\alpha_2$, and wherein the rear foot support portion is flexibly connected to the foot support.

14. An ankle-foot orthosis according to claim 1, wherein the elastic portion is elastic in use, to such an extent that when the angle $\alpha$ increases beyond the angle value $\alpha_2$ said elastic plantar flexion limiting means will exert a force that drives back the foot to the angle $\alpha$ substantially equal to the angle value $\alpha_2$.

15. An ankle-foot orthosis according to claim 1, wherein the elastic portion extends from one side of the foot support to an other side opposite the one side of the foot support in use.

16. An ankle-foot orthosis according to claim 15, wherein the elastic portion includes at least one elastic strap connected to the foot support, wherein the at least one elastic strap extends from one side of the foot support to a side of the lower leg support on the side of an other side opposite the one side of the foot support.

17. An ankle-foot orthosis according to claim 16, wherein the elastic portion includes at least two elastic straps connected to the foot support, which straps extend crosswise over the foot in use.

18. An ankle-foot orthosis according to claim 1, wherein plantar flexion limiting device is configured to preventing a foot from twisting inward, seen from a user's viewpoint, relative to an associated ankle joint.

19. An ankle-foot orthosis according to claim 1, wherein the plantar flexion limiting device is configured to preventing a foot from twisting outward, seen from a user's viewpoint, relative to an associated ankle joint.

20. An ankle-foot orthosis according to claim 19, wherein the non-elastic portion is configured to prevent the foot from twisting inward, seen from a user's viewpoint, relative to an associated ankle joint and wherein the elastic portion is configured to prevent the foot from twisting outward, seen from a user's viewpoint, relative to an associated ankle joint.

* * * * *